(12) United States Patent
Thistle

(10) Patent No.: US 10,610,250 B2
(45) Date of Patent: *Apr. 7, 2020

(54) TISSUE SHAVERS

(71) Applicant: DEPUY SYNTHES PRODUCTS, INC., Raynham, MA (US)

(72) Inventor: Robert C. Thistle, Bridgewater, MA (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 642 days.

This patent is subject to a terminal disclaimer.

(21) Appl. No.: 14/859,917

(22) Filed: Sep. 21, 2015

(65) Prior Publication Data

US 2016/0008020 A1 Jan. 14, 2016

Related U.S. Application Data

(63) Continuation of application No. 13/223,821, filed on Sep. 1, 2011, now Pat. No. 9,186,166.

(51) Int. Cl.
*A61B 17/32* (2006.01)
*A61B 17/00* (2006.01)

(52) U.S. Cl.
CPC ......... *A61B 17/32002* (2013.01); *A61B 2017/0023* (2013.01); *A61B 2017/0046* (2013.01); *A61B 2017/00238* (2013.01); *A61B 2017/00477* (2013.01); *A61B 2217/005* (2013.01)

(58) Field of Classification Search
CPC .... A61B 17/32002; A61B 2017/00477; A61B 2017/320064; A61B 2217/005
See application file for complete search history.

(56) References Cited

U.S. PATENT DOCUMENTS

| | | | |
|---|---|---|---|
| 4,203,444 A | 5/1980 | Bonnell et al. | |
| 4,649,919 A | 3/1987 | Thimsen et al. | |
| 5,084,052 A | 1/1992 | Jacobs | |
| 5,275,609 A | 1/1994 | Pingleton et al. | |
| 5,490,860 A | 2/1996 | Middle et al. | |

(Continued)

FOREIGN PATENT DOCUMENTS

| | | |
|---|---|---|
| JP | 54-077493 A | 6/1979 |
| JP | 2010-535535 A | 11/2010 |

(Continued)

OTHER PUBLICATIONS

Japanese Office Action for Application No. 2012-191340, dated Jul. 19, 2016 (14 pages).

(Continued)

*Primary Examiner* — Sarah W Aleman

(57) ABSTRACT

Various arthroscopic shavers are provided that minimize contact between bodily fluid and the shaver hand piece. Arthroscopic shavers generally include a cutting assembly mated to a hand piece. In one embodiment, the shaver includes a hub that connects the cutting assembly with the hand piece and has an exit port configured to transport cut tissue and fluid from the device. In another embodiment, the shaver includes a hub configured to retrofit existing shaver hand pieces having interior lumens for removing cut tissue and fluid. The hub further includes an exit port that diverts fluid away from the hand piece.

19 Claims, 17 Drawing Sheets

(56) References Cited

U.S. PATENT DOCUMENTS

| | | | |
|---|---|---|---|
| 5,529,580 A * | 6/1996 | Kusunoki | A61B 17/32002 604/22 |
| 5,569,284 A | 10/1996 | Young et al. | |
| 5,709,698 A * | 1/1998 | Adams | A61B 17/32002 604/22 |
| 5,871,493 A | 2/1999 | Sjostrom et al. | |
| 5,906,629 A | 5/1999 | Oren et al. | |
| 5,928,241 A * | 7/1999 | Menut | A61B 17/162 279/143 |
| 6,152,941 A | 11/2000 | Himes et al. | |
| 6,312,441 B1 | 11/2001 | Deng | |
| 7,237,990 B2 | 7/2007 | Deng | |
| 7,458,940 B2 | 12/2008 | Miller | |
| 7,510,563 B2 | 3/2009 | Cesarini et al. | |
| 7,559,927 B2 * | 7/2009 | Shores | A61B 17/162 606/79 |
| 7,850,620 B2 * | 12/2010 | Miller | A61B 10/025 600/568 |
| 7,922,737 B1 | 4/2011 | Cesarini et al. | |
| 8,906,053 B2 | 12/2014 | Oliver et al. | |
| 9,186,166 B2 | 11/2015 | Thistle | |
| 2004/0092992 A1 | 5/2004 | Adams et al. | |
| 2005/0065453 A1 | 3/2005 | Shabaz et al. | |
| 2005/0159677 A1 | 7/2005 | Shabaz et al. | |
| 2007/0045380 A1 | 3/2007 | Mastri et al. | |
| 2008/0243029 A1 | 10/2008 | Howard et al. | |
| 2011/0270256 A1 | 11/2011 | Nelson et al. | |
| 2014/0114291 A1 | 4/2014 | Defossez et al. | |

FOREIGN PATENT DOCUMENTS

| | | |
|---|---|---|
| WO | 94/18894 A1 | 9/1994 |
| WO | 2008/122057 A1 | 10/2008 |
| WO | 2010/146432 A1 | 12/2010 |
| WO | 2012/059228 A1 | 5/2012 |

OTHER PUBLICATIONS

European Search Report for application No. 12182668.9, dated Dec. 17, 2012. (9 pages).

* cited by examiner

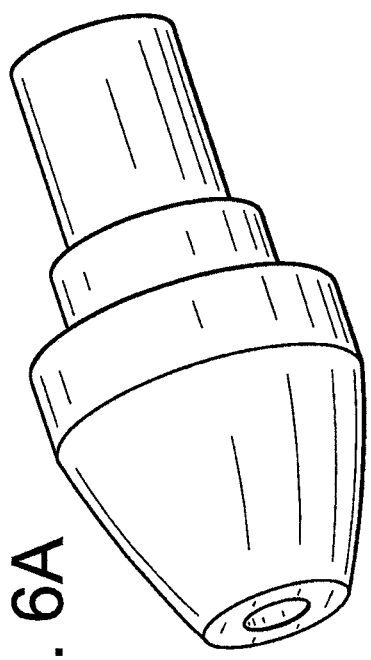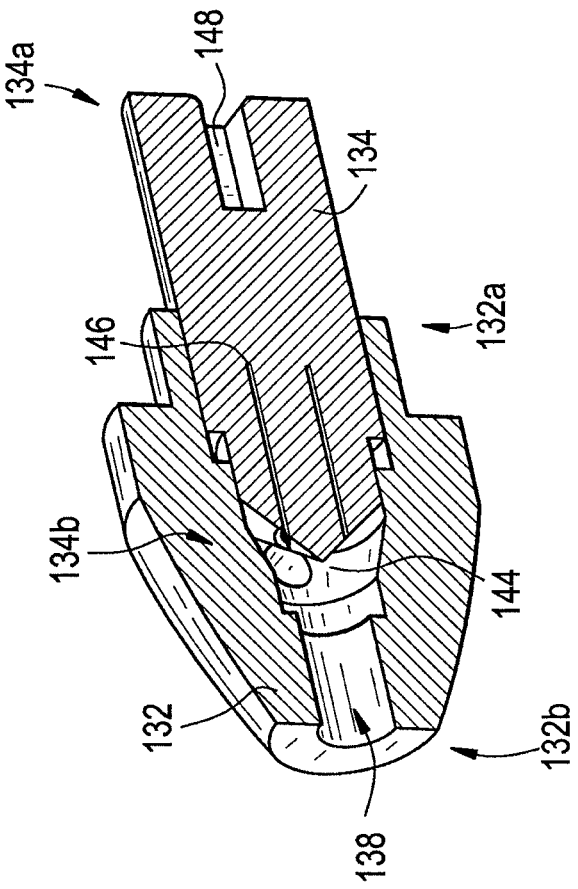

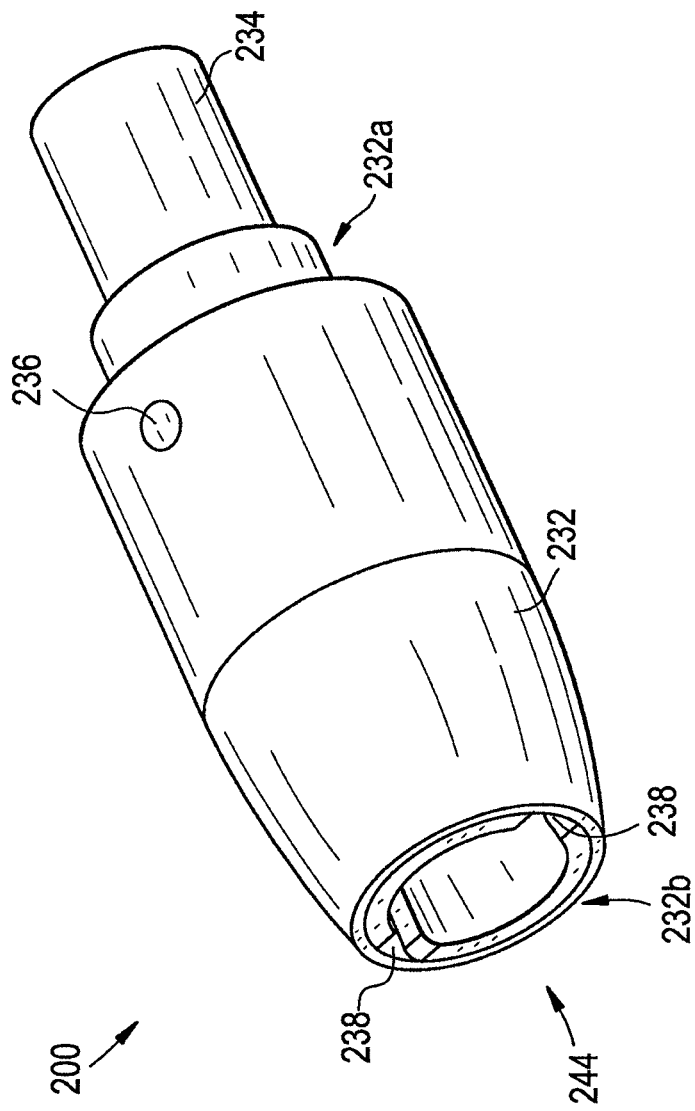

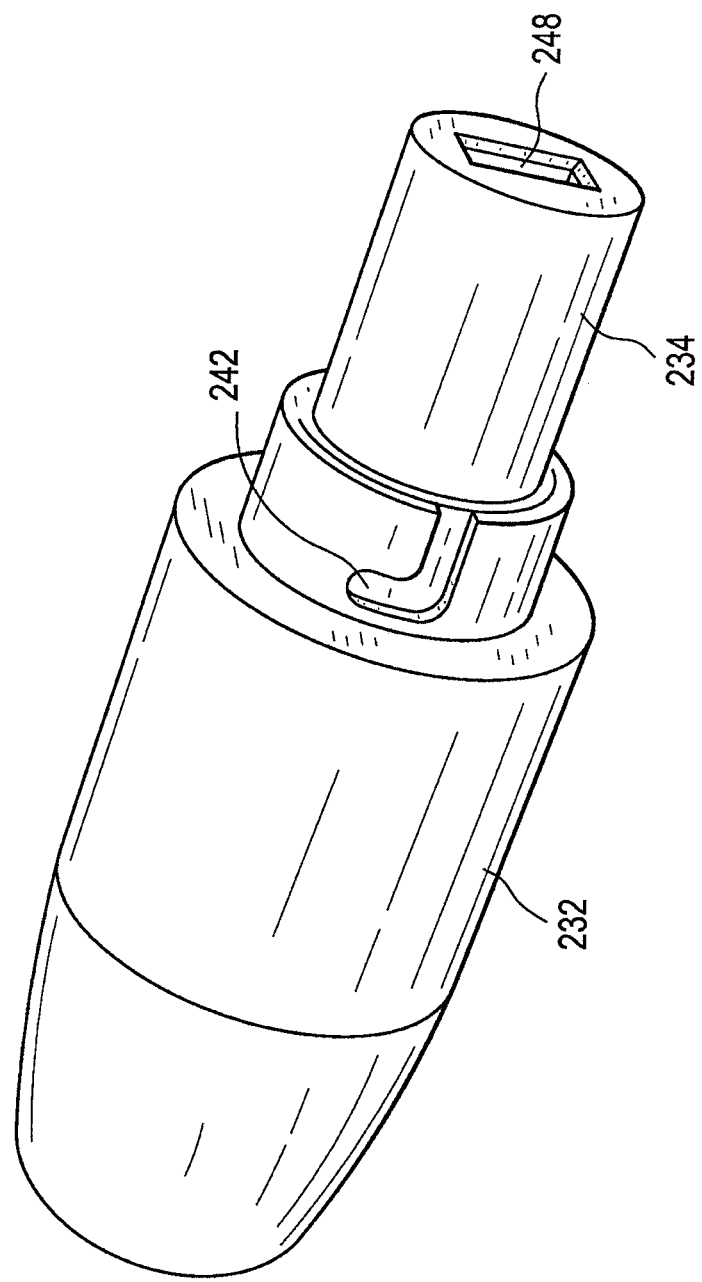

TISSUE SHAVERS

CROSS-REFERENCE TO RELATED APPLICATIONS

The present application is a continuation of U.S. application Ser. No. 13/223,821, filed Sep. 1, 2011, entitled "Tissue Shavers", the disclosure of which is incorporated herein by reference in its entirety.

FIELD

The present invention relates to endoscopic shavers for cutting and removing tissue from the body and methods of using the same.

BACKGROUND

Arthroscopy is a minimally invasive technique for removing diseased or damaged tissue from intra-articular regions of the body, such as the shoulder, hip, wrist, knee, and spine. Arthroscopic shavers can be used to remove bone, cartilage, and other soft tissue from a patient's joint with less surgical trauma to the joint than conventional surgical techniques. Typically, an arthroscopic shaver is an electro-mechanical device that includes a hand piece and a cutting assembly. The cutting assembly often has an elongate, rotatable member for cutting tissue and removing tissue and fluid from a surgical site. The shaver hand piece usually has an integrated aspiration/suction port for transferring tissue and fluid through the hand piece and to a waste collection container. The hand piece can be releasably mated to the cutting assembly so that the cutting assembly can be disposed of after each use.

During an arthroscopic procedure, the cutting assembly of the shaver is inserted into a small incision. Suction is applied to a suction port that extends through the handle, causing bodily tissue and associated fluids to flow through the cutting assembly and out through a proximal end of the hand piece. After the procedure is completed, the shaver blade is typically disposed of while the hand piece is sent to a processing center for cleaning and sterilization. Because fluid and tissue can become lodged inside of the hand piece, the hand piece must be thoroughly cleaned after each use through an aggressive series of brushing operations and/or using automated washing machines. Although the brushing is necessary to remove biological material from the hand piece, it can decrease the durability of the mechanical components and damage the seals within the shaver hand piece. There is also evidence that these conventional cleaning techniques are ineffective at removing biological material. The United States Food and Drug Administration has investigated the cleaning of the shaver hand pieces and found numerous cases where tissue has remained in the shavers after cleaning, compromising the sterility of a surgical site.

Accordingly, there remains a need for a tissue shaver that is easier to clean and that has a decreased risk of contaminating a surgical site.

SUMMARY

The present invention provides various embodiments of arthroscopic shavers. In one embodiment, a cutting assembly for use with a shaver hand piece is provided that includes an outer shaft having an outer cutting tip formed on a distal end thereof and an inner shaft rotatably disposed within the outer shaft and configured to coupled to a driver. The inner shaft can include an inner tissue cutting tip formed on its distal end. The cutting assembly can further include a hub coupled to the inner and outer shafts and configured to releasably mate with a handle assembly having a driver disposed therein. The hub can also be configured to prevent fluid from coming into contact with a handle assembly when the hub is coupled to a handle assembly. Thus, tissue cut by the outer and inner cutting tips can flow through the inner shaft without ever contacting the handle assembly.

The cutting assembly can have a variety of features. For example, the cutting assembly can further include an exit port configured to allow fluid and tissue to pass therethrough and being positioned to prevent fluid and tissue from flowing out through a proximal end of the cutting assembly. The hub can further include a driver mating feature for releasably coupling to a driver disposed in a handle assembly, and a handle mating feature for releasably coupling to a handle assembly. In certain aspects, the inner shaft can include at least one port configured to allow fluid and tissue to pass therethrough. The exit port of the cutting assembly can also be positioned distal of the driver mating feature formed on a proximal end of the inner hub, and can have a central axis that extends transverse to a central axis of the inner and outer shafts. The distal end of the hub can be mated to a proximal end of the inner shaft. The hub can also be configured to mate to a driver such that the driver is effective to rotate the inner shaft relative to the outer shaft.

In another embodiment, an arthroscopic tissue shaver can include a handle having a driver, a shaft assembly, and a coupler operably connected between the handle and the shaft assembly. The shaft assembly can include an outer shaft and an inner shaft having at least one opening formed in their respective distal ends and the inner shaft being rotatably disposed within the outer shaft. The inner shaft can further include a tissue cutting distal tip positioned adjacent to the at least one opening in the outer shaft for cutting tissue exposed through the opening. The coupler can operably connect the handle and the shaft assembly and it can transfer a drive force from the driver to the inner shaft. The coupler can also include an exit port for receiving fluid from an inner lumen of the inner shaft and it can be configured to prevent passage of the fluid from the inner lumen of the inner shaft to the handle.

The arthroscopic tissue shaver can have various configurations. For example, in one embodiment the coupler includes a proximal end mated to the driver in the handle, and a distal end mated to a proximal end of the inner shaft such that actuation of the driver is effective to rotate the inner shaft. The coupler can also be removably connected to the handle and to the shaft assembly. In another embodiment, the shaft assembly and the coupler are integrally formed. The coupler can also have an inner lumen formed therein, a first end in communication with the inner lumen of the inner shaft, and a second end in communication with the exit port. In one embodiment, the inner lumen of the coupler can terminate at a location distal of a proximal end of the coupler.

Another embodiment provides a connector for use with a tissue shaver. In this embodiment, the connector includes a housing having proximal and distal ends. The proximal end of the connector can have a drive feature for coupling to a driver disposed in a handle of the tissue shaver. Similarly, the distal end of the connector can have a drive feature for coupling to a corresponding drive feature on a proximal end of an inner shaft of a tissue shaver. The housing of the connector can further include a lumen that extends between an entry port formed in the distal end of the housing for receiving fluid from an inner shaft of a tissue shaver, and an exit port formed in a sidewall of the housing at a location distal to the proximal end of the housing for directing fluid away from a handle of a tissue shaver. The proximal end of the housing can also include a first mating feature formed thereon and configured to press-fit with a handle of a tissue shaver, and the distal end of the housing can include a second mating featured formed thereon and configured to press-fit with a shaft assembly of a tissue shaver.

BRIEF DESCRIPTION OF THE DRAWINGS

The invention will be more fully understood from the following detailed description taken in conjunction with the accompanying drawings, in which:

FIG. 6A is a perspective view of the outer hub of FIGS. 4A and 4B mated to the inner hub of FIGS. 5A-5C;

FIG. 6B is a cross-sectional view of the hub assembly shown in FIG. 6A;

FIG. 12A is a perspective view of a connector of the tissue shaver of FIG. 11, showing an exit port formed therein;

FIG. 12C is another perspective view of the connector of FIGS. 12A and 12B showing a mating feature that can mate to a shaver hand piece and a driver mating element;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides a tissue shaver that is configured to minimize contact between tissue/bodily fluid and the shaver hand piece. In general, an arthroscopic shaver is provided for removing tissue and reshaping a patient's anatomy, and can include a shaft assembly for cutting tissue and a reusable shaver hand piece. In one embodiment, the shaft assembly has a hub that connects the shaft assembly to the hand piece and that has an exit port for removing tissue and/or fluid from the device. In another embodiment, a connector is provided that can couple to the shaft assembly. The connector can have an exit port for removing tissue and/or fluid from the device. In an exemplary embodiment, the exit ports of the various embodiments disclosed herein are positioned so as to prevent cut tissue and/or fluid from coming into contact with the driver and other elements in the hand piece. For example, the hub and the connector, and thus the exit ports, can be positioned distal to the shaver hand piece so that fluid and/or tissue are prevented from flowing into the hand piece, making it easier to sterilize the hand piece after each use.

Figure 1:
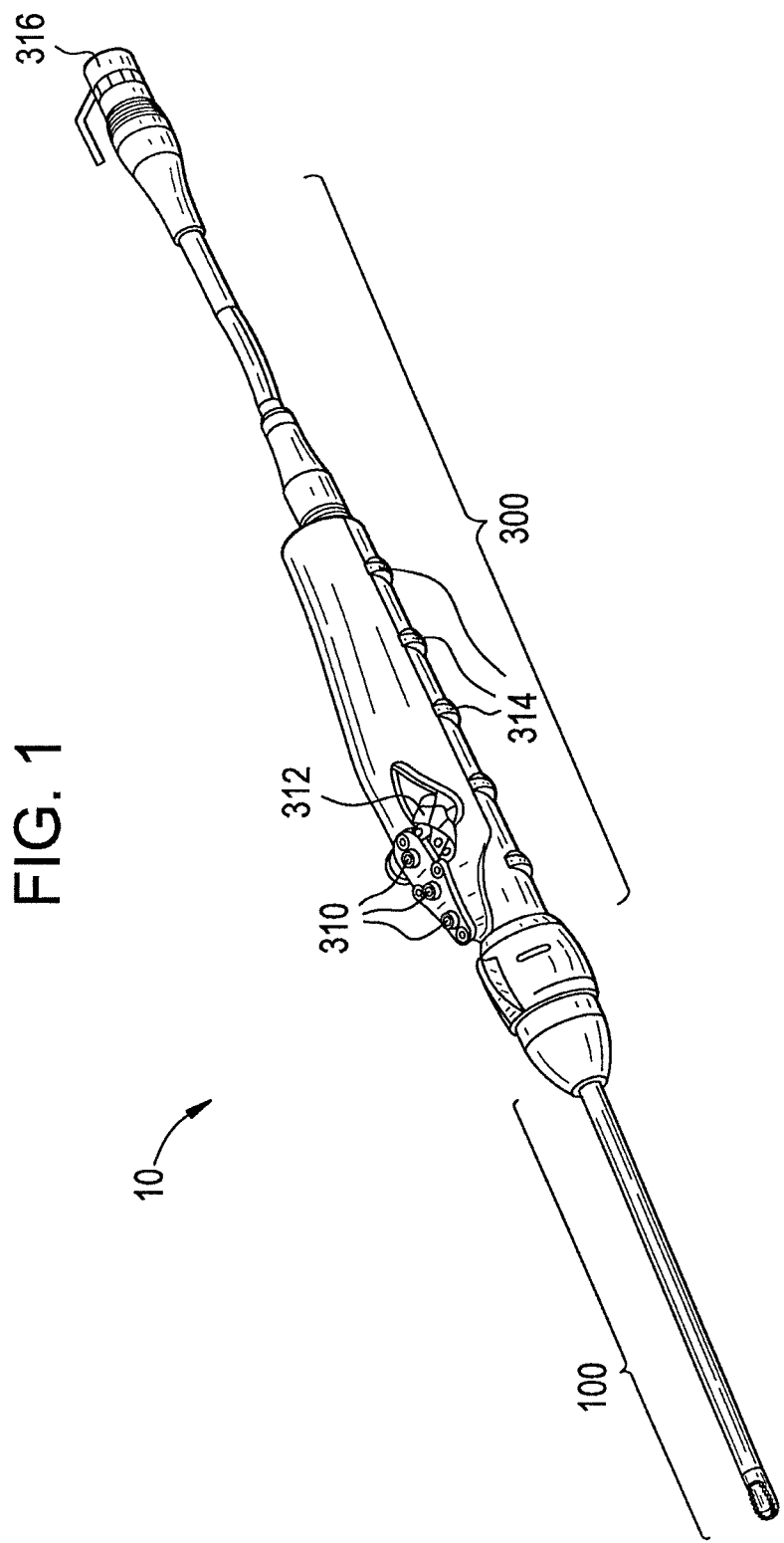
FIG. 1 is a perspective view of one embodiment of a tissue shaver.

FIG. 1 illustrates one embodiment of a tissue shaver 10. As shown, the arthroscopic tissue shaver 10 generally includes a hand piece 300 and a cutting assembly 100. The hand piece 300 can be configured to be grasped by a user and it can include various drivers and actuators for controlling the cutting assembly 100. The cutting assembly 100 can be configured to sever and transport tissue away from a surgical site.

While the shaver hand piece 300 can have a variety of configurations, it is preferably configured to facilitate grasping of the device 10 and to allow operation of the device with one hand. In the illustrated embodiment, the hand piece 300 is elongate with a generally cylindrical shape and includes surface features 314 that can provide friction between a user's hand and the hand piece 300. The hand piece 300 can house a driver (not shown) that can be operably connected to the cutting assembly 100 such that engagement of the driver causes the cutting assembly 100 to sever tissue. The driver can include a drive shaft (not shown) positioned in a central bore of the handle and that can extend toward a distal end of the hand piece 300 and can mate with a variety of cutting assemblies known in the art. The driver can further include a motor operably coupled to the drive shaft such that engagement of the motor causes the drive shaft to rotate. The hand piece 300 can be configured to connect to an external power source that can supply power to the motor, for example via socket 316. The hand piece 300 can further include an actuator, such as one or more buttons 310, for actuating the driver. The buttons 310 can provide signals to a processor that controls the motor and the buttons 310 can have a variety of functions. For example, each button 310 can cause the motor to operate in a different mode, such as a forward mode, reverse mode, or an oscillating mode, or the buttons 310 can have multiple functions depending upon the speed in which a user presses them. The hand piece can also include an actuator, e.g. a rotatable handle 312, for engaging a valve (not shown) that controls the application of suction to the cutting assembly, or alternatively, suction can be applied and controlled using a separate device. The hand piece 300 can also integrate with a fluid management system, such as the FMS Duo®+ of DePuy Mitek, Inc. In certain aspects, the hand piece 300 can be configured to be autoclaved without damaging the functionality of the motor so that the hand piece 300 can be sterilized after each use. A person skilled in the art will appreciate that hand piece can have a variety of configurations and various hand piece assemblies known in the art can be used with the present invention.

Figure 2:
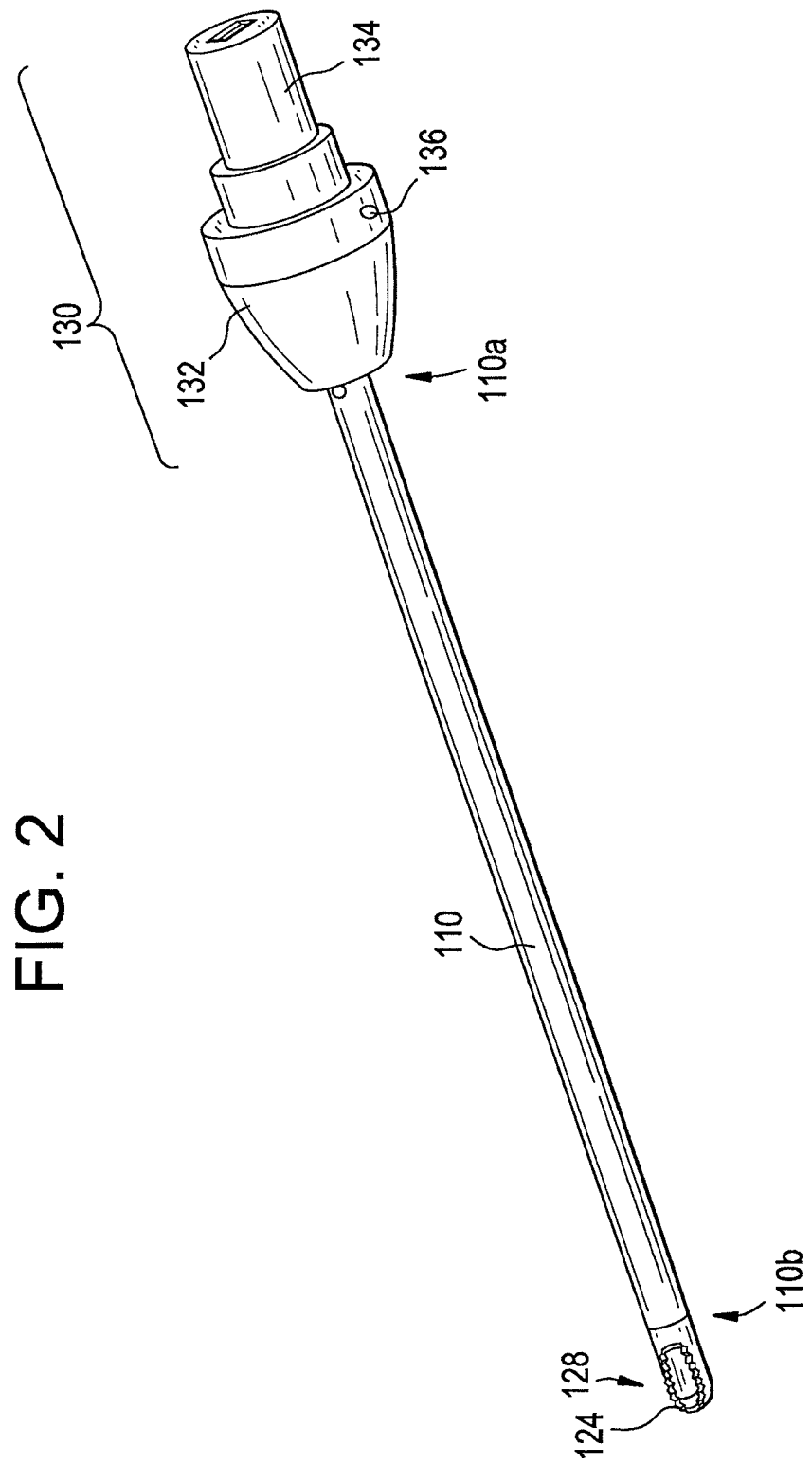
FIG. 2 is a perspective view of a cutting assembly of the tissue shaver of FIG. 1.
Figure 3:
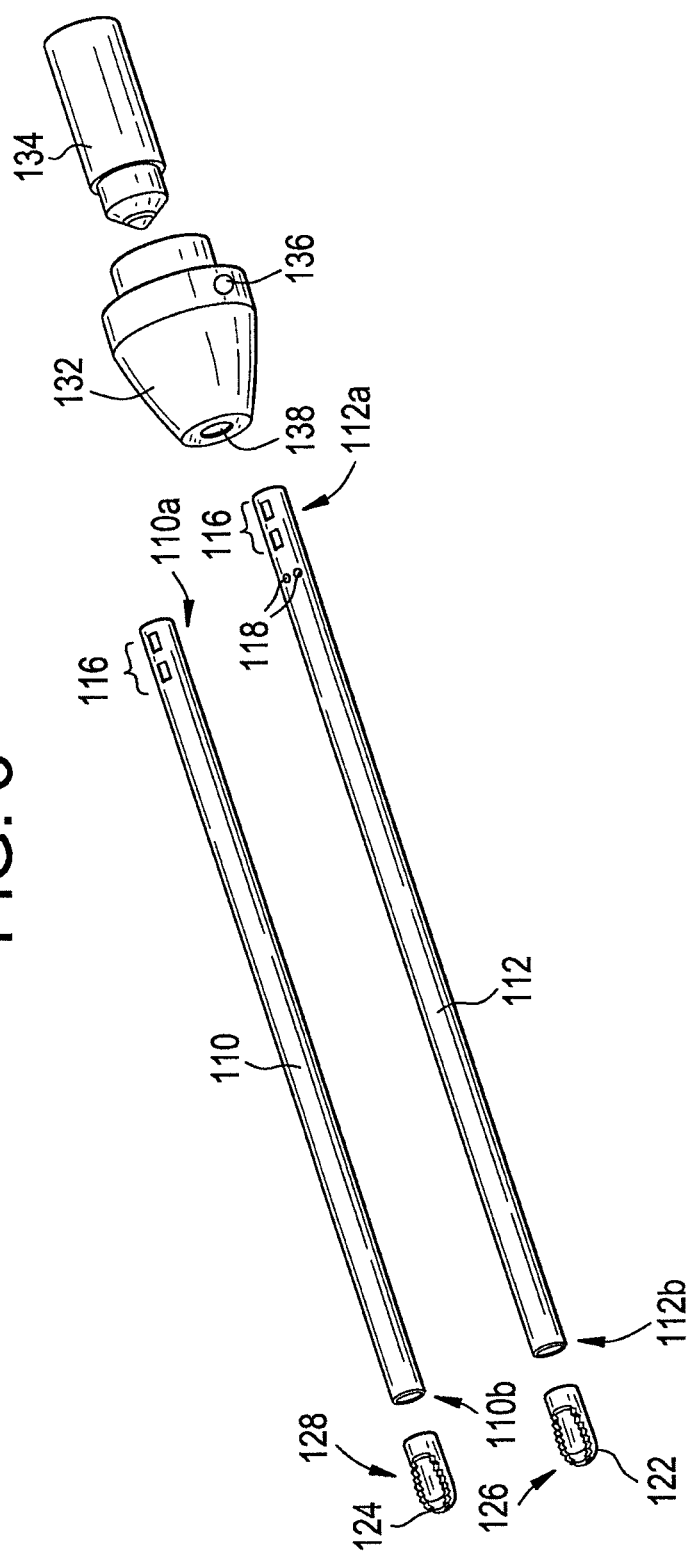
FIG. 3 is an exploded perspective view of the cutting assembly of FIG. 2.

FIGS. 2 and 3 show the cutting assembly 100 of the arthroscopic shaver of FIG. 1 in more detail. As explained above, the cutting assembly 100 is configured to cut and remove tissue from a surgical site. In the illustrated embodiment, the cutting assembly 100 generally includes outer and inner shafts 110, 112 and a hub assembly 130. The outer shaft 110 can be mated to an outer cutting element 124 and similarly, the inner shaft 112 can be mated to an inner cutting element 122. The inner shaft 112 can be configured to rotate relative to the outer shaft 110 to thereby cut tissue. As shown, the hub assembly 130 can mate the shafts 110, 112 to the shaver hand piece 300 and can include an exit port 136 for receiving tissue and/or fluid from the shafts 110, 112. A person skilled in the art will appreciate that the cutting assembly can include different components and can have a variety of other configurations for cutting and receiving tissue.

Figure 4A:
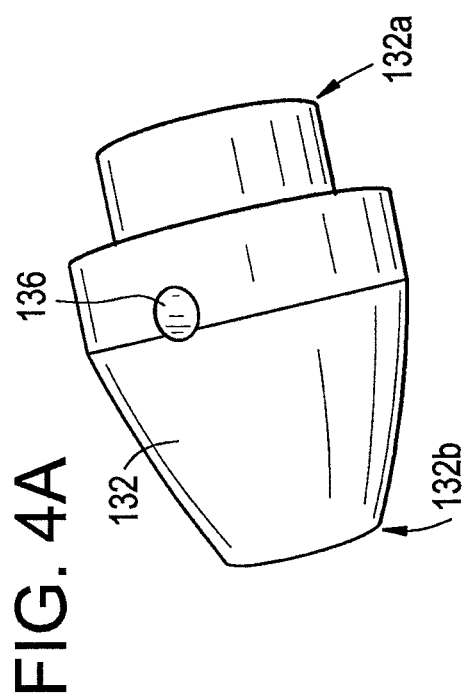
FIG. 4A is a side view of an outer hub of the cutting assembly of FIG. 2, showing an exit port formed therein.
Figure 4B:
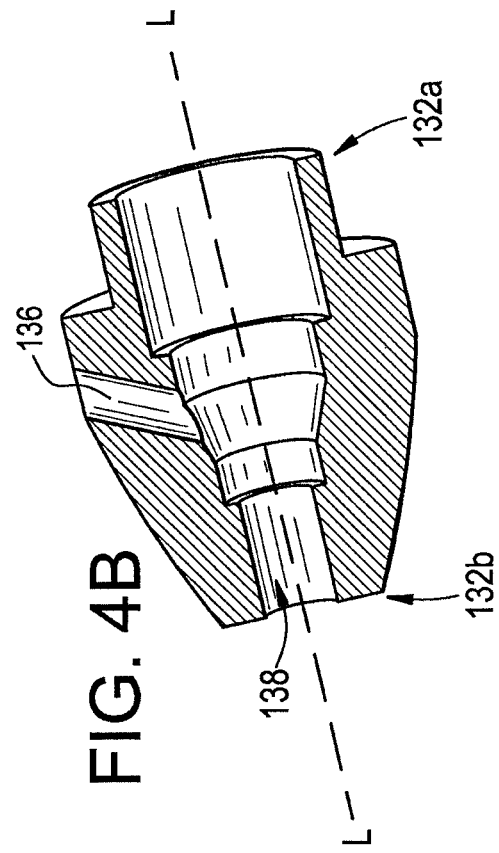
FIG. 4B is a cross-sectional view of the outer hub of FIG. 4A.

The hub assembly 130 can have various configurations, but in one embodiment, as shown, the hub assembly 130 includes an outer hub 132 and an inner hub 134. FIGS. 4A-4B show the outer hub 132 in more detail. While the shape of the outer hub 132 can vary, the illustrated hub has a generally frustoconical shape at a distal end 132b with a reduced-diameter cylindrical portion at a proximal end 132a. The distal end of the outer hub 132 can be configured to fixedly and non-rotatably mate to the outer shaft 110. Various mating techniques can be used, as will be discussed in more detail below with respect to the outer shaft 110. The proximal end of the outer hub 132 can be configured to mate to the hand piece 300. Various mating techniques known in the art can be used, such as welding, adhesives, a mechanical engagement, etc. The outer hub 132 also has a lumen 138 that extends along a central axis L between the proximal and distal ends 132a, 132b for transporting tissue and fluid from a surgical site. An exit port 136 can extend between the lumen 138 and an outer sidewall of the outer hub 132. The angle of the exit port 136 relative to the central axis L can vary, e.g. the exit port can extend perpendicular to the axis L, or it can extend at an acute or obtuse angle, as shown. A person skilled in the art will appreciate that the exit port 136 can have a variety of other configurations. The hub assembly can also be formed from a variety of different materials, including by way of non-limiting example, surgical grade stainless steel, titanium, and plastics.

Figure 5C:
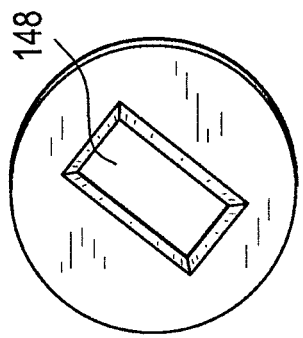
FIG. 5C is an end view of the inner hub of FIGS. 5A and 5B showing a mating element configured to mate with a hand piece.
Figure 5B:
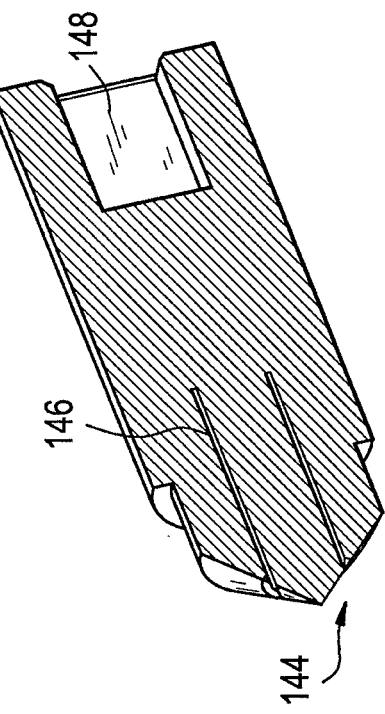
FIG. 5B is a cross-sectional view of the inner hub of FIG. 5A.
Figure 5A:
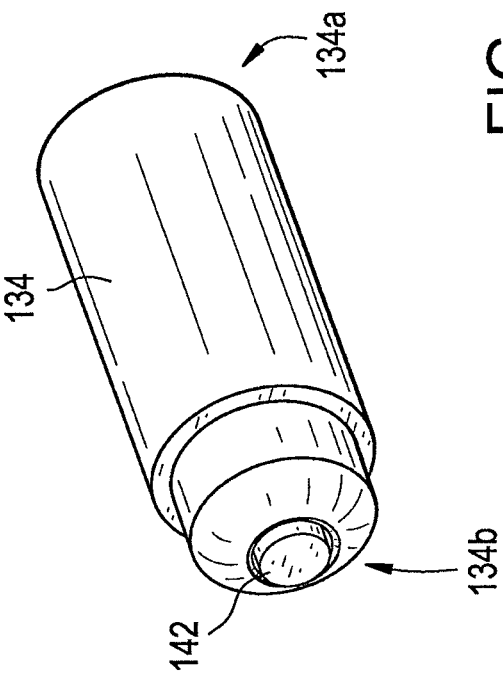
FIG. 5A is a perspective view of an inner hub of the cutting assembly of FIG. 2, showing a mating element configured to mate to the inner shaft.

As explained, the hub assembly 130 can also include an inner hub 134 that can mate to the inner shaft 112 and can rotatably couple to the outer hub 132. FIGS. 5A-5C show different views of the inner hub 134 of FIG. 2. While the inner hub 134 can have a variety of configurations, in the illustrated embodiment the inner hub 134 is a generally cylindrical member having a proximal end 134a and a distal end 134b. The inner hub 134 can have a larger diameter portion on its proximal end 134a and a smaller diameter cylindrical portion on its distal end 134b so that its proximal end 134a can mate to the shaver hand piece 300 and its distal end 134b can seat in a portion of the outer hub 132. The smaller diameter portion can taper distally and can terminate at a pointed distal tip 144. The distal end 134b of the inner hub 134 can have a mating feature 142 for mating with the inner shaft 112. While various mating features can be used, in one embodiment the mating feature can be in the form of a circular slot that extends from the distal end 134b of the hub 134 to an interior portion of the hub 134, as shown in FIGS. 5A-5B. This mating feature 142 can be configured to receive a proximal end 112a of the inner shaft 112, as will be described in more detail. As shown in FIG. 5C, the proximal end 134a of the inner hub 134 can include a driver mating feature 148 for mating with a driver disposed in the shaver hand piece 300 such that engagement of the driver causes rotation of the inner hub 134. In the illustrated embodiment, the driver mating feature 148 is in the form of a rectangular socket, however any form of mating feature known in the art can be used.

The inner and outer hubs 134, 132 can be mated, as shown in FIGS. 6A and 6B. In the illustrated embodiment, the distal end 134b of the inner hub 134 is inserted into the lumen 138 in the proximal end 132a of the outer hub 132, and it can be secured by a press-fit. A person skilled in the art will appreciate that the inner hub 134 can be secured to the outer hub 132 in a variety of other ways. In a preferred embodiment, the exit port 136 is unobstructed by other components, such as inner hub 134, so that tissue and/or fluid can flow through the exit port 136. For example, in the illustrated embodiment the distal end 134b of the inner hub 134 has a pointed distal tip 144 that terminates proximal to the exit port 136 so that tissue and fluid can readily flow through the exit port 136 and out of the device.

Figure 7A:
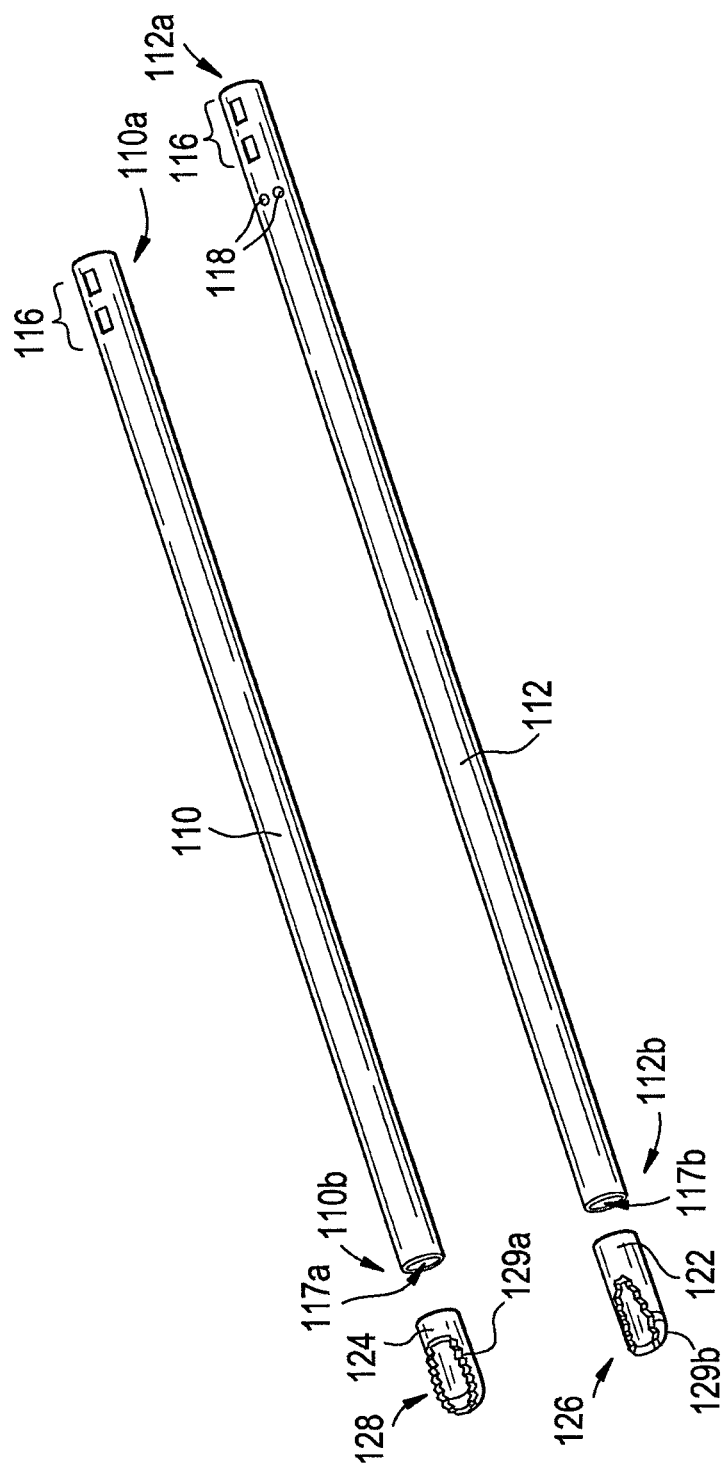
FIG. 7A is an exploded perspective view of the inner and outer shafts of FIG. 3.
Figure 7B:
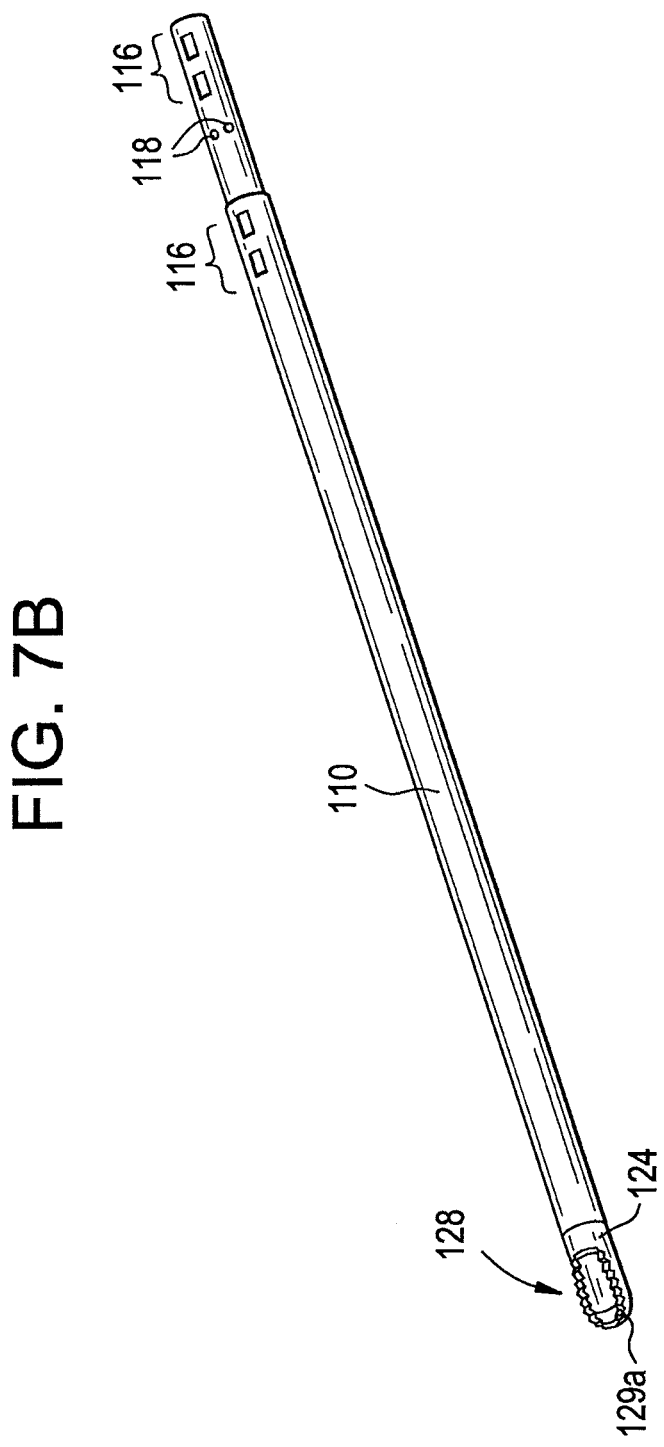
FIG. 7B is a perspective view of the inner and outer shafts of FIG. 7A mated to one another.

The cutting assembly 100, and in particular the inner and outer shafts 112, 110 for cutting and transferring tissue and/or fluid from a surgical site, can also have a variety of configurations. FIGS. 7A and 7B show the shafts in greater detail. In general, the inner and outer shafts 112, 110 are elongate members having proximal ends 112a, 110a, distal ends 112b, 110b, and inner lumen 117a, 117b extending therethrough. Both shafts can include features, such as a plurality of friction elements 116, configured to fixedly secure the shaft within the hub assembly 130 using a press-fit. Various other mating techniques known in the art can be used to secure the shafts 110, 112 within the hub assembly 130, such as welding, adhesives, a mechanical engagement, or any other technique. The inner shaft 112 can be configured to rigidly and non-rotatably mate to the inner hub 134 and can optionally be integrally formed as a single component such that the inner shaft 112 and the inner hub 134 are configured to move together as a unit. Similarly, the outer shaft 110 can be configured to rigidly and non-rotatably mate to the outer hub 132 and can be integrally formed as a single component. In the illustrated embodiment, the inner shaft 112 has a length that is greater than a length of the outer shaft 110, and the inner shaft 112 has an outer diameter that is less than an inner diameter of the outer shaft 110 so that it can rotate within the outer shaft. The inner shaft 112 can further include ports 118 for transferring tissue and fluid from the inner shaft 112 to the exit port 136 disposed in the outer hub 132. The ports 118 are preferably positioned at a location proximal to the proximal end 110a of the outer shaft 110, when the device is assembled, so that the outer shaft 110 does not block fluid flow through the ports 118.

As further shown, the distal ends 112b, 110b of the inner and outer shafts 112, 110 can also be configured to mate with an inner cutting member 122 and an outer cutting member 124, respectively. While the cutting members 122, 124 can have a variety of configurations, they are preferably configured to excise adjacent tissue from a surgical site. In the illustrated embodiment, the cutting members 122, 124 have a substantially cylindrical shape and include elliptical shaped openings 126, 128 that extend through an outer sidewall. The openings 126, 128 can have serrated teeth 129a, 129b on their circumference for cutting tissue.

Figure 8:
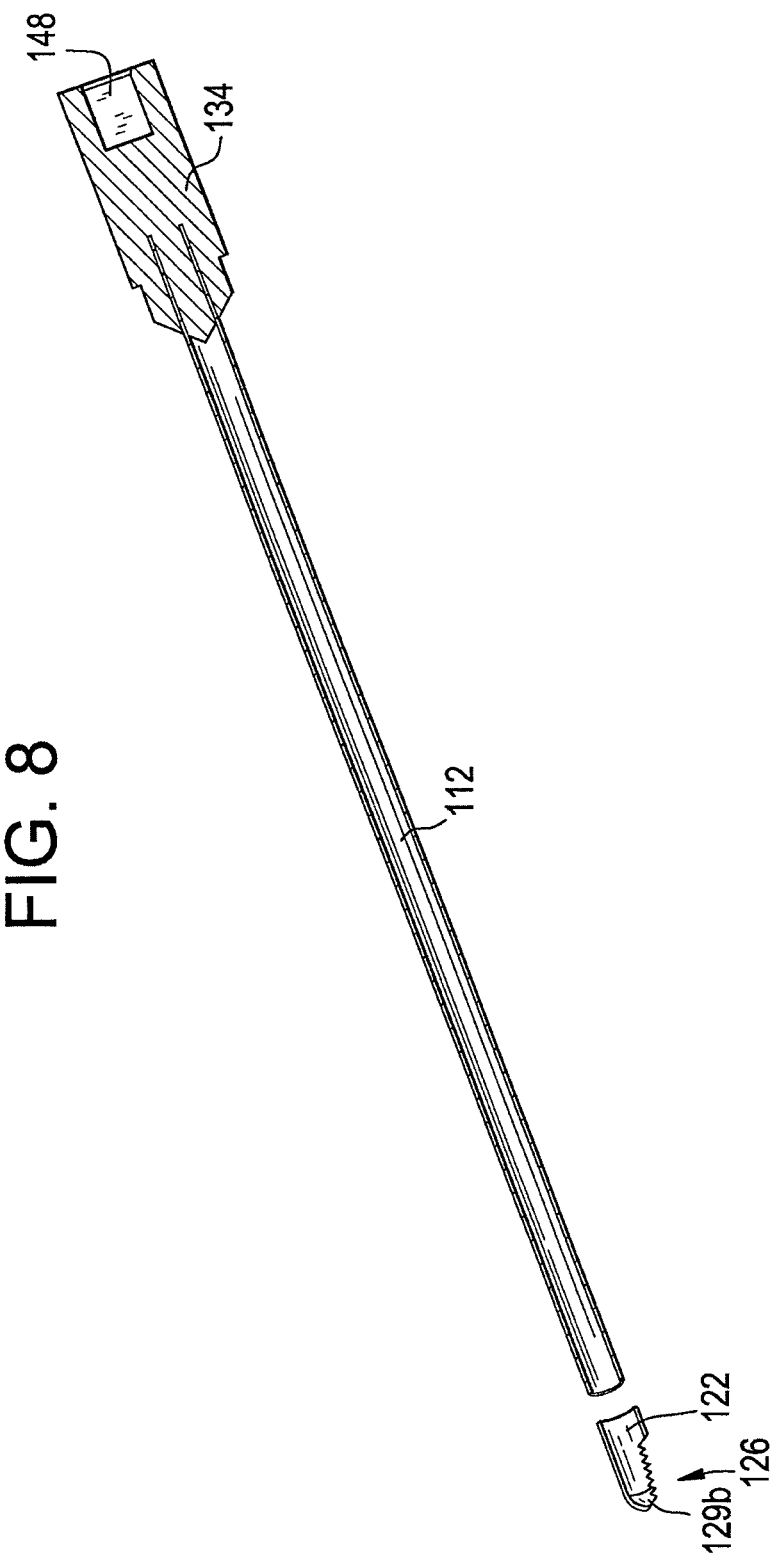
FIG. 8 is a partially-exploded cross-sectional view of the inner hub of FIGS. 5A-C mated to the inner shaft of FIG. 3.
Figure 9:
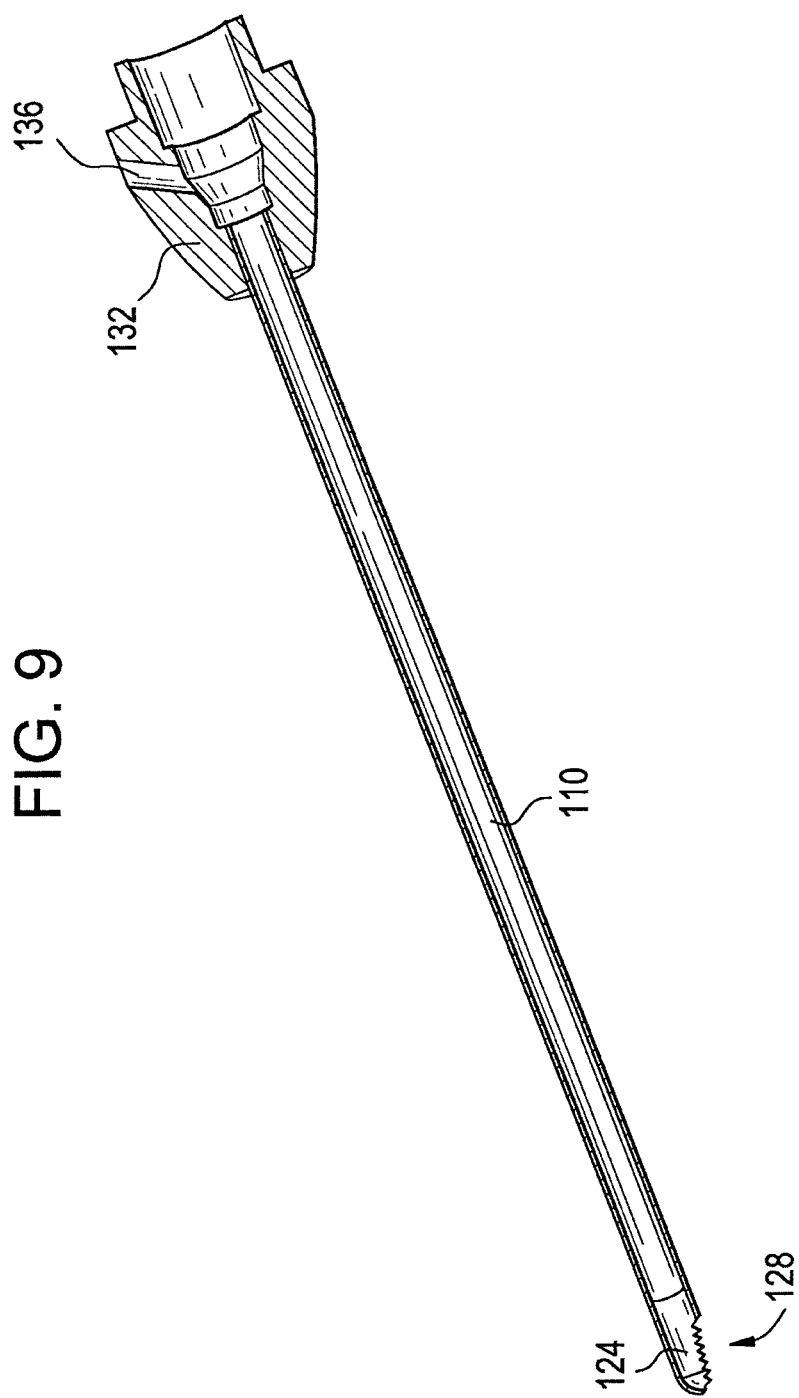
FIG. 9 is a cross-sectional view of the outer hub if of FIG. 4A mated to the outer shaft.
Figure 10:
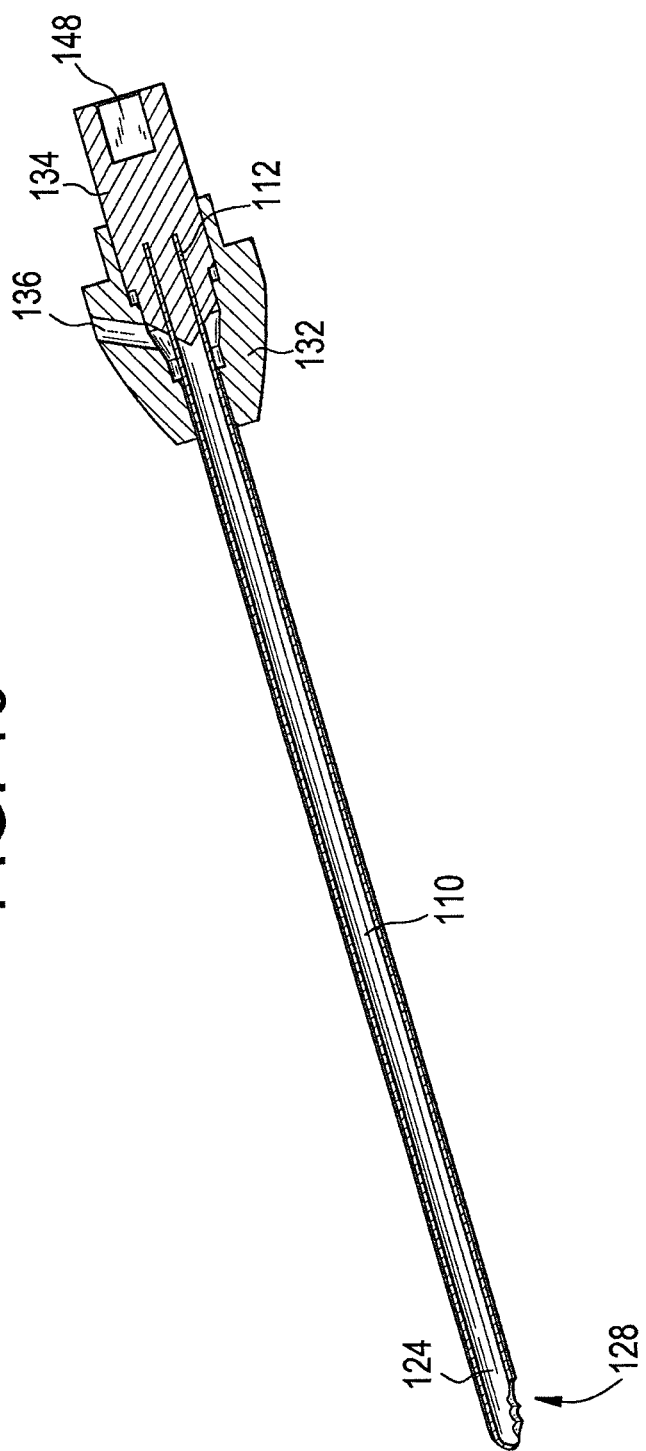
FIG. 10 is a cross-sectional view of the shaft and hub assembly of FIG. 2.

The components of the arthroscopic shaver of FIG. 1 can be assembled during the manufacturing process or by a user. For example, the inner shaft 112 can be mated with the inner hub 134 and the outer shaft 110 can be mated with the outer hub 132, as shown in FIGS. 8 and 9, respectively. The distal end 112b of the inner shaft 112 can be inserted into the proximal end 132a of the outer hub 132 and through the outer shaft 110 until the components are secured by a press-fit, as illustrated in FIG. 10. In the alternative, the shafts 110, 112 and hubs 132, 134 can be integrally formed during the manufacturing process. In both embodiments, the outer and inner hubs 132, 134 can be mated to the distal end 300a of the shaver hand piece 300 by a press-fit or using other mating techniques, e.g. using threads, or other mechanical techniques. In addition, the driver mating feature 148 on the proximal end 132a of the inner hub 134 can mate to a driver disposed in the shaver hand piece 300 so that engagement of the driver causes rotation of the inner hub 134. In particular, a shaft of the driver can be keyed to extend into and engage the mating feature 148 so that the driver can thereby effect rotation of the inner hub 134 and inner shaft 112. After a procedure is complete, the cutting assembly 100 can be disengaged from the hand piece 300 and disposed of, while the hand piece 300 can be cleaned and reused. A person skilled in the art will appreciate that the components of the tissue shaver can be assembled in numerous ways and using a variety of securing mechanisms.

In use, the cutting assembly 100 of the tissue shaver 20 can be inserted into an incision made in a patient. Optionally, the depth of the cutting assembly 100 within the incision can be monitored using fluoroscopy, X-ray, or other visualization techniques known in the art. After the cutting assembly 100 is positioned at the desired depth, suction can be applied through exit port 136. Tissue adjacent to the outer cutting member 124 is drawn through the openings 128, 126, respectively. The actuators 310 on the shaver hand piece 300 can be depressed or otherwise activated, which causes the inner shaft 112 to rotate relative to the outer shaft 100. Because the shafts are non-rotatably coupled to the cutting members 122, 124, inner cutting member 122 rotates relative to the outer cutting member 110 and the tissue trapped in the inner cutting member 122 is cut by the serrated teeth 129a, 129b. The applied suction causes the cut tissue and/or fluid to flow through the lumen 117b in the inner shaft 112 and out through exit port 136 formed in the outer hub 132. The cut tissue and/or fluid can be collected in a suitable waste collection container. This process can be repeated until the desired amount of tissue is excised from the surgical site. After the procedure is complete, the cutting assembly 100 can be disengaged from the hand piece 300 and disposed of, while the hand piece 300 can be cleaned and reused.

Figure 11:
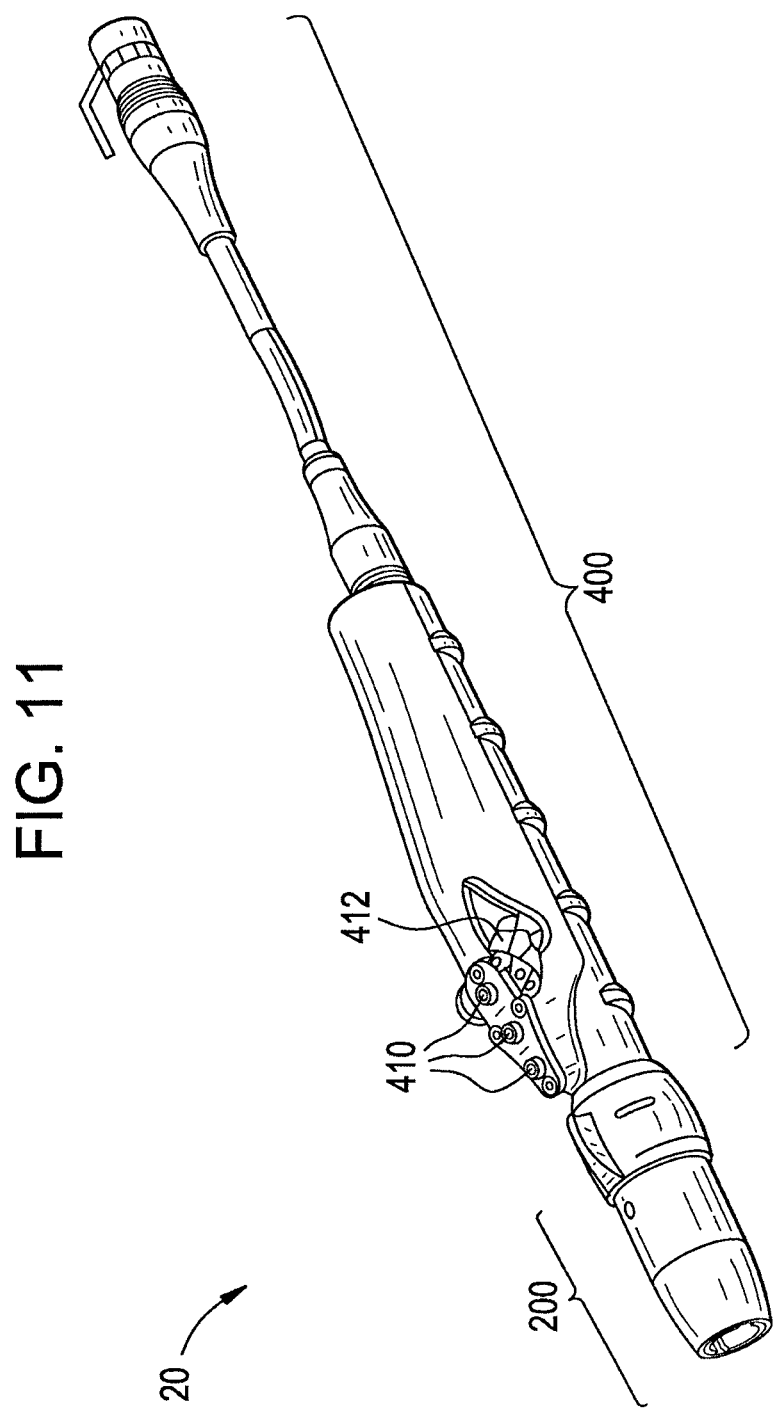
FIG. 11 is a perspective view of another embodiment of a tissue shaver.

Components are also provided for retrofitting existing shaver hand pieces that have an inner lumen for removing fluid and tissue from the device. For example, in one embodiment a tube can be inserted in the inner lumen of a hand piece and can extend between proximal and distal ends of the hand piece. A distal end of the tube can be mated with a proximal end of the cutting assembly, such as a proximal end of an inner shaft, and a proximal end of the tube can be coupled to a waste collection container. Preferably, the cutting assembly and the tube have a fluid-tight connection that prevents tissue and fluid from directly contacting the inner lumen of the hand piece. As shown in FIG. 11, in another embodiment a tissue shaver 20 can include a cutting assembly (not shown), a connector 200, and a hand piece 400. The connector 200 can connect a cutting assembly to the hand piece 400 and can prevent tissue and fluid from entering the exit port in the shaver hand piece 400. More specifically, one end of the connector 200 can mate to a cutting assembly and the other end can mate to a hand piece 400. The connector 200 can divert tissue and/or fluid away from the shaver hand piece 400 and thereby minimize contact between the biological material and the shaver hand piece 400. In both of the embodiments, tissue and bodily fluid is prevented from directly contacting a shaver hand piece, making cleaning and sterilization of the hand piece simpler and more effective.

Figure 12B:
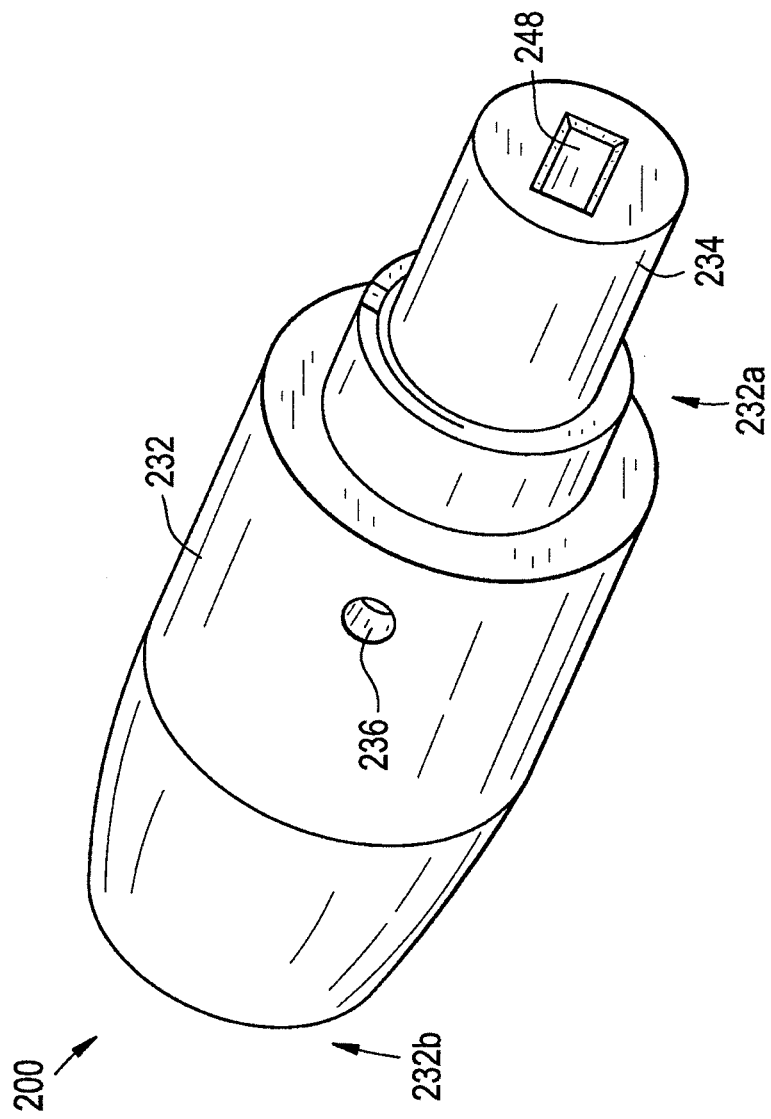
FIG. 12B is a perspective view of the connector of FIG. 12A showing a mating element configured to mate to a driver disposed in a shaver hand piece.

FIGS. 12A-12C illustrate the connector 200 of FIG. 11 in greater detail. The connector 200 can mate to a cutting assembly and to a shaver hand piece 400, and can divert tissue away from the hand piece 400. In the illustrated embodiment, the connector 200 is a substantially cylindrical component that includes tubular-shaped outer and inner hubs 232, 234. The outer and inner hubs 232, 234 operably connect the cutting assembly to the shaver hand piece 400 and prevent tissue from contacting the shaver hand piece 400. The outer hub 232 further includes an exit port 236 for diverting tissue from entering the hand piece 400. As shown in FIG. 12A, the outer hub 232 has a lumen 244 that extends between the proximal and distal ends 232a, 232b. The exit port 236 extends between the lumen 244 and an outer sidewall of the outer hub 232. The inner hub 234 blocks the proximal end of the lumen in the outer hub 232, such that fluid is forced to flow through the exit port 236 and is prevented from flowing into the hand piece (not shown). The position of the exit port 236 can vary, but it is preferably located distal to the proximal end 232a of the outer hub 232, and distal to the distal end 234b of the inner hub 234 when the hubs are assembled so that the inner hub 234 does not obstruct the exit port 236. A person skilled in the art will appreciate that the outer and inner hubs can be formed from a variety of different materials and can have a variety of configurations.

Figure 13:
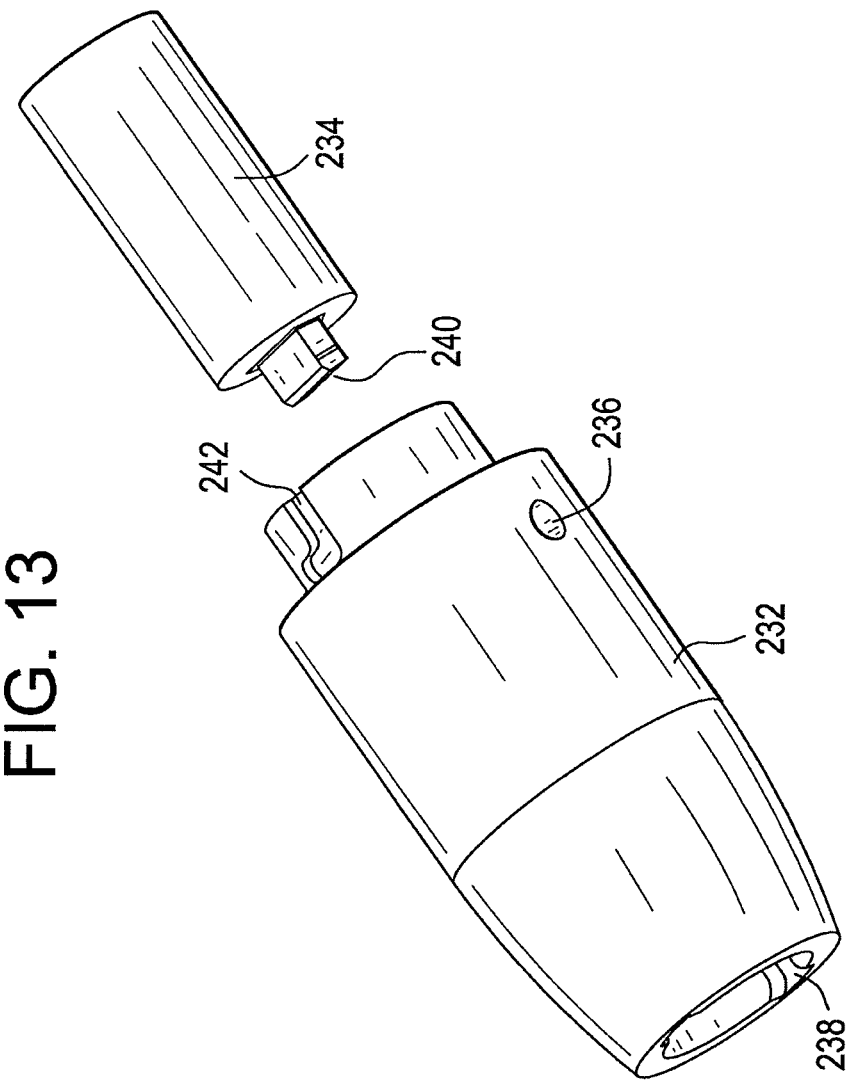
FIG. 13 is an exploded view of the connector of FIGS. 12A and 12B.

Because the connector 200 is an intermediary component positioned between the shaver hand piece 400 and the cutting assembly, the driver disposed in the shaver hand piece 400 will not directly mate with the cutting assembly. Instead, the outer and inner hubs 232, 234 are configured to transfer a drive force between the hand piece 400 and the cutting assembly such that actuation of the driver disposed in the hand piece 400 causes the cutting assembly to sever tissue. As shown in FIGS. 12B and 12C, the inner hub 232 can include a driver mating feature 248 at a proximal end for mating to a driver disposed in the shaver hand piece 400. The inner hub 234 can further include a protrusion 240, shown in FIG. 13, at a distal end 234b for mating directly to a portion of a cutting assembly, such as a shaft. Alternatively, an intermediate component (not shown) can join the inner hub 234 to the cutting assembly such that rotation of the inner hub 234 causes rotation of the cutting assembly. FIGS. 12A-14 also show the outer hub 232, which has two mating features 242 that can mate to corresponding features on the shaver hand piece 400. In the illustrated embodiment, the hand piece 400 can be guided toward the proximal end 230a of the hub 230, and a distal portion of the hand piece 400 can seat in slot 247a. The hand piece 400 can further include protrusions that correspond to mating features 242 so that the hand piece 400 can be twist-locked and secured to the connector 200. FIG. 13 is an exploded view of the connector 200 that shows the components in more detail. A person skilled in the art will appreciate that the connector can have a variety of configurations and can include a variety of mating features configured to join the connector with a cutting assembly and a shaver hand piece.

Figure 14:
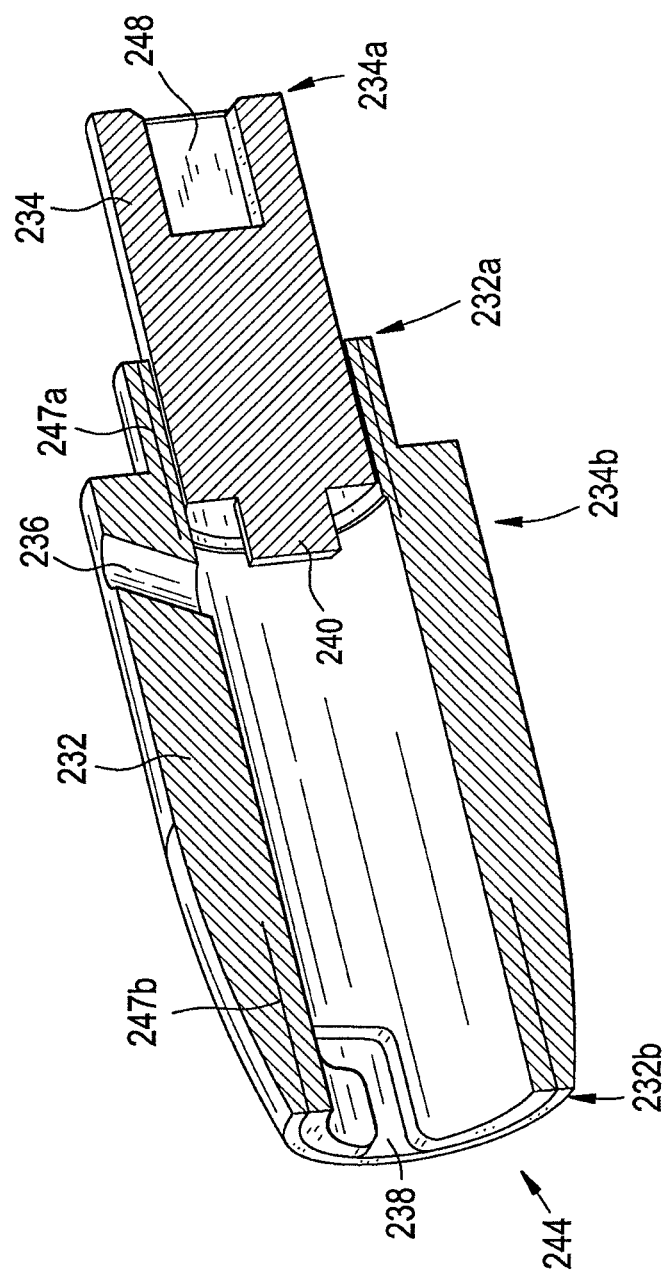
FIG. 14 is a cross-sectional view of the connector of FIGS. 12A and 12B.

As shown in FIG. 14, the outer hub 232 can include mating elements 238 on its distal end 232b for mating to a cutting assembly. In the illustrated embodiment, the mating elements 238 are substantially L-shaped depressions formed in an inner sidewall of the outer hub 232. Corresponding protrusions on the cutting assembly can engage the mating elements 238 and the cutting assembly can be secured to the outer hub 232 using a twist-lock. A portion of the cutting assembly can also be seated in slot 247b formed in the outer hub 232 to allow rotation of the cutting assembly relative to the outer hub 232, and thus the connector 200, as will be discussed below. A person skilled in the art will appreciate that the cutting assembly can be secured to the connector by various other means known in the art.

FIG. 14 also shows a cross-section of the inner hub 234 mated to the outer hub 232 by a press-fit. The inner hub 234 can be mated to the outer hub 232 by various other mating techniques known in the art, such as welding, adhesives, a mechanical engagement. In the illustrated embodiment, the inner hub 234 is positioned so that the exit port 236 is unobstructed by the inner hub 234. Preferably, when the cutting assembly is attached to the outer hub 232 there is space in the inner lumen 244 of the outer hub 232 for tissue and/or fluid to flow through the inner lumen 244 and out through the exit port 236. In addition, the protrusion 240 of the inner hub 234 preferably terminates at a location proximal to the exit port 236 to allow tissue and fluid to readily flow through the exit port 236. A person skilled in the art will appreciate that the angle of the exit port 236 relative to the lumen 244 can vary, e.g. the exit port 236 can extend perpendicular to the lumen 244 or it can extend at an acute or obtuse angle.

The arthroscopic shaver of FIG. 11 functions similar to the embodiment shown in FIG. 1. In use, the cutting assembly (not shown) of the tissue shaver 20 can be inserted into an incision made in a patient. The position of the cutting assembly can be monitored using a variety of visualization techniques known in the art, such as X-ray imaging. Suction can be applied to the cutting assembly at exit port 236 disposed in the connector 200. The applied suction draws tissue adjacent to the cutting members through their respective openings and into an inner lumen. The actuators 410 on the shaver hand piece 400 can be depressed, causing the cutting assembly to sever the tissue disposed in the inner lumen of the cutting assembly, such as by the rotation of inner and outer cutting elements. Actuation of the driver causes the inner hub 234 to rotate relative to the outer hub 232. Because the inner hub 234 has a protrusion 240 that is operably coupled to the inner shaft of the cutting assembly, rotation of the inner hub 234 causes the inner shaft to rotate relative to the outer hub and an outer shaft, thereby severing tissue. The cut tissue and/or fluid to flows through the lumen of the cutting assembly and out through the exit port 236 formed in the outer hub 232 of the connector 200. Rather than allowing tissue and/or fluid to flow through an inner lumen in the shaver hand piece 400, the connector 200 diverts this material away from the shaver hand piece 400 and out through exit port 236. Because tissue and fluid is prevented from entering the hand piece 400, the hand piece 400 is easier to clean and has a decreased risk of cross-contaminating a surgical site. The cut tissue and/or fluid can be collected in a suitable waste collection container and the process can be repeated until the desired amount of tissue is excised from the surgical site. Similar to the embodiment shown in FIG. 1, after the procedure is complete, the cutting assembly can be removed from the connector 200 and disposed of, and the connector 200 can be removed from the shaver hand piece 400. The shaver hand piece 400 and/or the connector 200 can be cleaned and reused, if desired.

As will be appreciated by a person skilled in the art, the tissue shavers provided can be used to remove tissue from various regions in the body, including by way of non-limiting example, shoulder, hip, wrist, knee, and spine.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An arthroscopic tissue shaver device, comprising:
   a handle having a driver and an internal passageway, the internal passageway extending between proximal and distal ends of the handle and being configured for receiving fluid therethrough;
   a shaft assembly having an outer shaft and an inner shaft, the inner and outer shafts each having at least one distal opening, and the inner shaft having a tissue cutting distal tip positioned adjacent to the at least one distal opening of the outer shaft for cutting tissue extending through the opening; and
   a coupler having an inner hub and an outer hub, the coupler for transferring a drive force from the driver to the inner shaft, the coupler having each of a shaft mating feature for releasably mating with a proximal end of the outer shaft of the shaft assembly, an exit port for diverting fluid received from the inner shaft out of the device, a distally extending protrusion disposed at a distal end of the inner hub that terminates at a distal-facing surface of the inner hub, the distal-facing surface being substantially perpendicular to a coupler longitudinal axis that extends through a length of the coupler, the coupler longitudinal axis extending in a direction that is substantially parallel to or aligned with a shaft longitudinal axis that extends through a length of at least one of the inner shaft and the outer shaft, the distally extending protrusion being adapted to releasably mate with a proximal end of the inner shaft by positioning the proximal end of the inner shaft around the protrusion, and a driver mating feature configured to releasably mate with a corresponding mating feature on the driver,
   wherein the coupler is configured to retrofit the handle to prevent fluid from flowing out of the inner lumen of the inner shaft and into the internal passageway in the handle.

2. The device of claim 1, wherein the exit port is configured to allow fluid and tissue to pass therethrough.

3. The device of claim 1, wherein the exit port has a central axis that extends substantially transverse to a central axis of the inner and outer shafts.

4. The device of claim 1, wherein the outer shaft is configured to press-fit with the coupler.

5. The device of claim 1, wherein the coupler has an inner lumen formed therein having a first end in communication with the inner lumen of the inner shaft, and a second end in communication with the exit port.

6. The device of claim 1, wherein the internal passageway of the handle extends along a central longitudinal axis of the handle between the proximal and distal ends.

7. The device of claim 1, wherein the inner shaft includes at least one port configured to allow fluid and tissue to pass therethrough.

8. The device of claim 7, wherein the at least one port directs fluid through the exit port of the coupler.

9. The device of claim 1, wherein the distal end of the inner hub further comprises a recess formed between the distal-facing surface and the protrusion to receive a portion of the inner shaft therein.

10. A connector for retrofitting a tissue shaver that directs fluid through a proximal end of a handle, the connector comprising:
a housing having an inner hub and an outer hub, the inner hub having a proximal end that includes a drive feature for coupling to a driver disposed in a handle of a tissue shaver to which the connector is coupled, and the outer hub having each of a lumen formed in the outer hub for receiving fluid from an inner shaft of a shaft assembly of a tissue shaver to which the connector is coupled, a first mating feature configured to releasably mate with a corresponding mating feature on an outer shaft of a shaft assembly of a tissue shaver to which the connector is coupled, and an exit port for directing fluid away from a handle of a tissue shaver to which the connector is coupled,
wherein the inner hub is configured for releasably mating with a proximal end of an inner shaft of a shaft assembly of a tissue shaver to which the connector is coupled,
wherein an exterior surface of a proximal end of the outer hub has a reduced diameter portion, the reduced diameter portion being configured to allow a tapered distal end of the inner hub to pass through the proximal end, the reduced diameter portion having an inner wall configured to abut an outer wall of the inner hub at a first location along a length of the inner hub to secure the inner hub to the outer hub, the inner hub having a substantially uniform diameter from the first location to the proximal end of the inner hub,
wherein the inner hub is configured to rotate relative to the outer hub to transfer a rotating drive force from a driver of a tissue shaver to which the connector is coupled to an inner shaft of that same tissue shaver, and
wherein the inner wall is configured to abut the tapered distal end of the inner hub at a second location along the length of the inner hub to secure the inner hub to the outer hub, a distance between the second location and a central longitudinal axis of the outer hub being smaller than a distance between the first location and the central longitudinal axis of the outer hub.

11. The connector of claim 10, wherein the proximal end of the outer hub has a second mating feature configured to press-fit with a handle of a tissue shaver to which the connector is coupled.

12. The connector of claim 11, wherein the first and second mating features formed on the outer hub comprise longitudinal slots extending in a proximal to distal direction.

13. The connector of claim 10, wherein the proximal end of the inner hub is sealed to prevent tissue and fluid flowing through the lumen in the housing from contacting a handle of a tissue shaver to which the connector is coupled.

14. The connector of claim 10, wherein the lumen is in communication with the exit port for directing fluid through the outer hub and out of the exit port.

15. The connector of claim 10, wherein the inner wall abuts the outer wall of the inner hub at the first location and the tapered distal end of the inner hub at the second location simultaneously.

16. A method of assembling a tissue shaver, comprising:
detaching a first inner shaft of a shaft assembly of a tissue shaver from an inner rotatable hub associated with a coupler of the tissue shaver;
coupling a second inner shaft of the shaft assembly to the inner rotatable hub, the second inner shaft taking the place of the detached first inner shaft; and
coupling a driver of a handle assembly of the tissue shaver to a proximal end of the inner rotatable hub such that a drive force from the driver can be transferred from the driver to the inner hub, and thus to the second inner shaft;
wherein the coupler includes an exit port formed therein for diverting fluid out of the coupler, and
wherein coupling the second inner shaft to the inner rotatable hub includes positioning the second inner shaft over a protrusion that extends to a distal-most point of the inner rotatable hub and engaging the protrusion with the second inner shaft to couple the second inner shaft to the inner rotatable hub.

17. The method of claim 16, wherein the handle assembly includes an inner passageway extending therethrough between proximal and distal ends and the step of coupling the second inner shaft of the shaft assembly to the inner rotatable hub provides a path for fluid to travel through the second inner shaft and out of the exit port.

18. The method of claim 16, wherein the coupler is a separate component from the tissue shaver such that prior to attaching the coupler to the handle assembly of the tissue shaver, no fluid path exists between the second inner shaft and tissue shaver to allow fluid to be evacuated from the second inner shaft.

19. The method of claim 16, wherein coupling the second inner shaft to the inner rotatable hub further comprises sliding the second inner shaft over the protrusion proximally along the protrusion such that the second inner shaft is received in a recess formed between a distal-facing surface of the inner rotatable hub from which the protrusion extends and the protrusion.

* * * * *